(12) United States Patent
Njoroge et al.

(10) Patent No.: US 11,959,048 B2
(45) Date of Patent: Apr. 16, 2024

(54) POLYETHYLENE GLYCOL PARTICLES INCLUDING BACTERIAL ENDOSPORES

(71) Applicant: The Procter & Gamble Company, Cincinnati, OH (US)

(72) Inventors: Samuel Kimani Njoroge, Cincinnati, OH (US); Julie Marie Porter, Amelia, OH (US); Neil Joseph Lant, Gosforth (GB)

(73) Assignee: The Procter & Gamble Company, Cincinnati, OH (US)

( * ) Notice: Subject to any disclaimer, the term of this patent is extended or adjusted under 35 U.S.C. 154(b) by 654 days.

(21) Appl. No.: 17/086,631

(22) Filed: Nov. 2, 2020

(65) Prior Publication Data
US 2021/0130737 A1    May 6, 2021

(30) Foreign Application Priority Data
Nov. 6, 2019 (EP) .................................... 19207354

(51) Int. Cl.
| | | |
|---|---|---|
| *C11D 17/06* | (2006.01) | |
| *C11D 3/00* | (2006.01) | |
| *C11D 3/37* | (2006.01) | |
| *C12N 1/20* | (2006.01) | |

(52) U.S. Cl.
CPC .......... *C11D 3/0068* (2013.01); *C11D 3/3707* (2013.01); *C12N 1/20* (2013.01)

(58) Field of Classification Search
CPC ..... C11D 17/06; C11D 17/065; C11D 17/047; C11D 11/0017; C11D 13/20; C11D 9/44; C11D 3/50; C11D 3/381; C11D 3/2065
See application file for complete search history.

(56) References Cited

U.S. PATENT DOCUMENTS

| | | | | |
|---|---|---|---|---|
| 2009/0105111 A1* | 4/2009 | Stolte | .................. | C11D 3/3707 510/392 |
| 2012/0076864 A1* | 3/2012 | Vandendaele | .......... | C11D 3/381 424/490 |
| 2013/0184196 A1* | 7/2013 | Brooke | .................. | A01N 63/22 510/461 |
| 2016/0051599 A1* | 2/2016 | Drahos | .................. | A23K 10/18 424/93.46 |
| 2017/0260481 A1* | 9/2017 | Vasquez Valdivieso | | ..................... C11D 3/50 |
| 2017/0340528 A1 | 11/2017 | Sodd | | |
| 2019/0002819 A1* | 1/2019 | Heffron | ................ | C11D 3/0068 |
| 2019/0048291 A1 | 2/2019 | Gori et al. | | |
| 2019/0264141 A1 | 8/2019 | Findeisen et al. | | |
| 2019/0284647 A1* | 9/2019 | Bach | ...................... | C12N 1/205 |

FOREIGN PATENT DOCUMENTS

| | | |
|---|---|---|
| JP | 2011500913 A | 1/2011 |
| JP | 2019513166 A | 5/2019 |

OTHER PUBLICATIONS

Search Report for appl. no 19207354.2-1105, dated May 7, 2020, 11 pages.
Wiwattanapatapee et al:Effervescent fast-disintegrating bacterial formulation for biological control of rice sheath plight, Journal of Controlled Release, Elsevier, Amsterdam, NL, vol. 119, No. 2, May 16, 2007 May 16, 2007, pp. 229-235, XP022080063, ISSN: 0168-3659, DOI 10.1016 J.JCONREL.2007.01 .015.
PCT Search Report and Written Opinion for PCT/US2020/070732 dated Mar. 25, 2021, 17 pages.
Extended EP Search Report and Written Opinion for 20205117.3 dated Mar. 25, 2021, 10 pages.

\* cited by examiner

*Primary Examiner* — Charles I Boyer

(57) ABSTRACT

A composition including a plurality of particles, wherein the particles comprise: at least 40% by weight of the particles of a non-germinant carrier; and from about 0.0001% to about 5% by weight of the particles of a bacterial composition including bacterial endospores; and wherein each of the particles has a mass between about 1 mg to about 5000 mg, preferably between about 5 mg and about 200 mg.

14 Claims, No Drawings

POLYETHYLENE GLYCOL PARTICLES INCLUDING BACTERIAL ENDOSPORES

FIELD OF THE INVENTION

The present invention is in the field of particulate laundry additive. In particular the invention relates to particles comprising bacterial endospores to reduce fabric malodor.

BACKGROUND OF THE INVENTION

Malodors on fabrics even after they have been washed seem to be a recurring problem. The objective of the present invention is to provide a product that ameliorates malodors on fabrics.

SUMMARY OF THE INVENTION

According to a first aspect of the invention, there is provided a laundry additive composition comprising a plurality of particles, wherein said particles comprise: at least 40%, preferably from about 45% to about 99.999% by weight of said particles of a non-germinant carrier; and from about 0.0001% to about 5% by weight of said particles of a bacterial composition comprising bacterial endospores; the particles preferably comprise from $1\times10^2$ to $1\times10^9$ CFU/g bacterial endospores, more preferably from $1\times10^3$ to $1\times10^6$ CFU/g of bacterial endospores. Each of said particles has a mass between about 1 mg to about 5000 mg, preferably between about 5 mg and about 200 mg.

According to the second aspect of the invention, there is provided a product comprising a container comprising the composition of the invention.

According to the third aspect of the invention, there is provided a process for treating soiled laundry articles comprising the steps of:
  treating the articles with a detergent composition; and
  treating the articles with the composition of the invention.

The endospores seem to deposit on the laundry articles during the wash and in the presence of heat seem to germinate and to reduce malodor. The endospores seem to be very useful in the case of for example sweaty items, that have been washed with the composition of the invention. The endospores seem to germinate in the presence of the complex soils produced during sweating and by the heat produced, the endospores reduce the malodor.

According to the fourth aspect of the invention, there is provided a process for forming particles comprising the steps of:
providing a precursor material; providing a distributor having a plurality of apertures; passing said precursor material through said apertures; providing a moving conveyor beneath said distributor; depositing said precursor material onto said moving conveyor; and cooling said precursor material to form a plurality of particles; wherein said precursor material preferably comprises polyethylene glycol, wherein said polyethylene glycol has a weight average molecular weight from about 2000 to about 13000; wherein said precursor material comprises from about 0.0001% to about 5% by weight of said precursor material of a bacterial composition comprising bacterial endospores; and wherein said precursor material is provided at a temperature less than about 70° C. It has surprisingly been found that the endospores do not germinate when subjected to this process.

Lately, there is provided the use of the composition of the invention to reduce malodors from fabrics.

The elements of the composition of the invention described in relation to the first aspect of the invention apply *mutatis mutandis* to the other aspects of the invention.

DETAILED DESCRIPTION OF THE INVENTION

All percentages, ratios and proportions used herein are by weight percent of the composition, unless otherwise specified. All average values are calculated "by weight" of the composition, unless otherwise expressly indicated. All ratios are calculated as a weight/weight level, unless otherwise specified.

All measurements are performed at 25° C. unless otherwise specified.

Unless otherwise noted, all component or composition levels are in reference to the active portion of that component or composition, and are exclusive of impurities, for example, residual solvents or by-products, which may be present in commercially available sources of such components or compositions.

Bacterial Endospores

Some gram-positive bacteria have a two-stage lifecycle in which growing bacteria under certain conditions such as in response to nutritional deprivation can undergo an elaborate developmental program leading to spores or endospores formation. The bacterial spores are protected by a coat consisting of about 60 different proteins assembled as a biochemically complex structure with intriguing morphological and mechanical properties. The protein coat is considered a static structure that provides rigidity and mainly acting as a sieve to exclude exogenous large toxic molecules, such as lytic enzymes. Spores play critical roles in long term survival of the species because they are highly resistant to extreme environmental conditions. Spores are also capable of remaining metabolically dormant for years. Methods for obtaining bacterial spores from vegetative cells are well known in the field. In some examples, vegetative bacterial cells are grown in liquid medium. Beginning in the late logarithmic growth phase or early stationary growth phase, the bacteria may begin to sporulate. When the bacteria have finished sporulating, the spores may be obtained from the medium, by using centrifugation for example. Various methods may be used to kill or remove any remaining vegetative cells. Various methods may be used to purify the spores from cellular debris and/or other materials or substances. Some example methods for producing bacterial spores are described in Example 1 of this disclosure. Bacterial spores may be differentiated from vegetative cells using a variety of techniques, like phase-contrast microscopy, automated scanning microscopy, high resolution atomic force microscopy or tolerance to heat, for example.

Because bacterial spores are generally environmentally-tolerant structures that are metabolically inert or dormant, they are readily chosen to be used in commercial microbial products. Despite their ruggedness and extreme longevity, spores can rapidly respond to the presence of small specific molecules known as germinant that signal favorable conditions for breaking dormancy through germination, an initial step in the process of completing the lifecycle by returning to vegetative bacteria. For example, the commercial microbial products may be designed to be dispersed into an environment where the spores encounter the germinants present in the environment, to germinate into vegetative cells and perform an intended function. A variety of different bacteria may form spores. Bacteria from any of these groups may be used in the compositions, methods, and kits disclosed herein. For example, some bacteria of the following genera may form endospores: *Acetonema, Alkalibacillus, Ammoniphilus, Amphibacillus, Anaerobacter, Anaerospora, Aneurinibacillus, Anoxybacillus, Bacillus, Brevibacillus, Caldanaerobacter, Caloramator, Caminicella, Cerasibacillus, Clostridium, Clostridiisalibacter, Cohnella, Dendrosporobacter, Desulfotomaculum, Desulfosporomusa, Desulfosporosinus, Desulfovirgula, Desulfunispora, Desulfurispora, Filifactor, Filobacillus, Gelria, Geobacillus, Geosporobacter, Gracilibacillus, Halonatronum, Heliobacterium, Heliophilum, Laceyella, Lentibacillus, Lysinibacillus, Mahella, Metabacterium, Moorella, Natroniella, Oceanobacillus, Orenia, Ornithinibacillus, Oxalophagus, Oxobacter, Paenibacillus, Paraliobacillus, Pelospora, Pelotomaculum, Piscibacillus, Planifilum, Pontibacillus, Propionispora, Salinibacillus, Salsuginibacillus, Seinonella, Shimazuella, Sporacetigenium, Sporoanaerobacter, Sporobacter, Sporobacterium, Sporohalobacter, Sporolactobacillus, Sporomusa, Sporosarcina, Sporotalea, Sporotomaculum, Syntrophomonas, Syntrophospora, Tenuibacillus, Tepidibacter, Terribacillus, Thalassobacillus, Thermoacetogenium, Thermoactinomyces, Thermoalkalibacillus, Thermoanaerobacter, Thermoanaeromonas, Thermobacillus, Thermoflavimicrobium, Thermovenabulum, Tuberibacillus, Virgibacillus,* and/or *Vulcanobacillus.*

In some examples, the bacteria that may form endospores are from the genus *Bacillus*. In various examples, the *Bacillus* bacteria may be strains of *Bacillus alcalophilus, Bacillus alvei, Bacillus aminovorans, Bacillus amyloliquefaciens, Bacillus aneurinolyticus, Bacillus aquaemaris, Bacillus atrophaeus, Bacillus boroniphilius, Bacillus brevis, Bacillus caldolyticus, Bacillus centrosporus, Bacillus cereus, Bacillus circulans, Bacillus coagulans, Bacillus firmus, Bacillus flavothermus, Bacillus fusiformis, Bacillus globigii, Bacillus infernus, Bacillus larvae, Bacillus laterosporus, Bacillus lentus, Bacillus licheniformis, Bacillus megaterium, Bacillus mesentericus, Bacillus mucilaginosus, Bacillus mycoides, Bacillus natto, Bacillus pantothenticus, Bacillus polymyxa, Bacillus pseudoanthracis, Bacillus pumilus, Bacillus schlegelii, Bacillus sphaericus, Bacillus sporothermodurans, Bacillus stearothermophillus, Bacillus subtilis, Bacillus thermoglucosidasius, Bacillus thuringiensis, Bacillus vulgatis, Bacillus weihenstephanensis,* or combinations thereof.

In some examples, the bacterial strains that form spores may be strains of *Bacillus*, including: *Bacillus* sp. strain SD-6991; *Bacillus* sp. strain SD-6992; *Bacillus* sp. strain NRRL B-50606; *Bacillus* sp. strain NRRL B-50887; *Bacillus pumiluss* train NRRL B-50016; *Bacillus amyloliquefaciens* strain NRRL B-50017; *Bacillus amyloliquefaciens* strain PTA-7792 (previously classified as *Bacillus atrophaeus*); *Bacillus amyloliquefaciens* strain PTA-7543 (previously classified as *Bacillus atrophaeus*); *Bacillus amyloliquefaciens* strain NRRL B-50018; *Bacillus amyloliquefaciens* strain PTA-7541; *Bacillus amyloliquefaciens* strain PTA-7544; *Bacillus amyloliquefaciens* strain PTA-7545; *Bacillus amyloliquefaciens* strain PTA-7546; *Bacillus subtilis* strain PTA-7547; *Bacillus amyloliquefaciens* strain PTA-7549; *Bacillus amyloliquefaciens* strain PTA-7793; *Bacillus amyloliquefaciens* strain PTA-7790; *Bacillus amyloliquefaciens* strain PTA-7791; *Bacillus subtilis* strain NRRL B-50136 (also known as DA-33R, ATCC accession No. 55406); *Bacillus amyloliquefaciens* strain NRRL B-50141; *Bacillus amyloliquefaciens* strain NRRL B-50399; *Bacillus licheniformis* strain NRRL B-50014; *Bacillus licheniformis* strain NRRL B-50015; *Bacillus amyloliquefaciens* strain NRRL B-50607; *Bacillus subtilis* strain NRRL B-50147 (also known as 300R); *Bacillus amyloliquefaciens* strain NRRL B-50150; *Bacillus amyloliquefaciens* strain NRRL B-50154; *Bacillus megaterium* PTA-3142; *Bacillus amyloliquefaciens* strain ATCC accession No. 55405 (also known as 300); *Bacillus amyloliquefaciens* strain ATCC accession No. 55407 (also known as PMX); *Bacillus pumilus* NRRL B-50398 (also known as ATCC 700385, PMX-1, and NRRL B-50255); *Bacillus cereus* ATCC accession No. 700386; *Bacillus thuringiensis* ATCC accession No. 700387 (all of the above strains are available from Novozymes, Inc., USA); *Bacillus amyloliquefaciens* FZB24 (e.g., isolates NRRL B-50304 and NRRL B-50349 TAEGRO® from Novozymes); *Bacillus subtilis* (e.g., isolate NRRL B-21661 in RHAPSODY®, SERENADE® MAX and SERENADE® ASO from Bayer CropScience); *Bacillus pumilus* (e.g., isolate NRRL B-50349 from Bayer CropScience); *Bacillus amyloliquefaciens* TrigoCor (also known as "TrigoCor 1448"; e.g., isolate Embrapa Trigo Accession No. 144/88.4Lev, Cornell Accession No. Pma007BR-97, and ATCC accession No. 202152, from Cornell University, USA) and combinations thereof.

In some examples, the bacterial strains that form spores may be strains of *Bacillus amyloliquefaciens*. For example, the strains may be *Bacillus amyloliquefaciens* strain PTA-7543 (previously classified as *Bacillus atrophaeus*), and/or *Bacillus amyloliquefaciens* strain NRRL B-50154, *Bacillus amyloliquefaciens* strain PTA-7543 (previously classified as *Bacillus atrophaeus*), *Bacillus amyloliquefaciens* strain NRRL B-50154, or from other *Bacillus amyloliquefaciens* organisms.

In some examples, the bacterial strains that form spores may be *Brevibacillus* spp., e.g., *Brevibacillus brevis; Brevibacillus formosus; Brevibacillus laterosporus*; or *Brevibacillus parabrevis*, or combinations thereof.

In some examples, the bacterial strains that form spores may be *Paenibacillus* spp., e.g., *Paenibacillus alvei; Paenibacillus amylolyticus; Paenibacillus azotofixans; Paenibacillus cookii; Paenibacillus macerans; Paenibacillus polymyxa; Paenibacillus validus*, or combinations thereof. The *Bacillus* spores may have an average particle diameter of about 2-50 microns, suitably about 10-45 microns. *Bacillus* spores are commercially available in blends in aqueous carriers and are insoluble in the aqueous carriers. Other commercially available *bacillus* spore blends include without limitation Freshen Free™ CAN (10×), available from Novozymes Biologicals, Inc.; Evogen® Renew Plus (10×), available from Genesis Biosciences, Inc.; and Evogen® GT (10×, 20× and 110×), all available from Genesis Biosciences, Inc. In the foregoing list, the parenthetical notations (10×, 20×, and 11 OX) indicate relative concentrations of the *Bacillus* spores.

Bacterial spores used in the compositions, methods, and products disclosed herein may or may not be heat activated. In some examples, the bacterial spores are heat activated. In some examples, the bacterial spores are not heat inactivated.

For the compositions disclosed here, populations of bacterial spores are generally used. In some examples, a population of bacterial spores may include bacterial spores from a single strain of bacterium. In some examples, a population of bacterial spores may include bacterial spores from 2, 3, 4, 5, or more strains of bacteria. Generally, a population of bacterial spores contains a majority of spores and a minority of vegetative cells. In some examples, a population of bacterial spores does not contain vegetative cells. In some examples, a population of bacterial spores may contain less than about 1%, 2%, 3%, 4%, 5%, 6%, 7%, 8%, 9%, 10%, 15%, 20%, 25%, 30%, 40%, or 50% vegetative cells, where the percentage of bacterial spores is calculated as ((vegetative cells/(spores in population+vegetative cells in population))×100). Generally, populations of bacterial spores used in the disclosed compositions are stable (i.e. not undergoing germination), with at least some individual spores in the population capable of germinating.

Populations of bacterial spores used in this disclosure may contain bacterial spores at different concentrations. In various examples, populations of bacterial spores may contain, without limitation, at least $1\times10^2$, $5\times10^2$, $1\times10^3$, $5\times10^3$, $1\times10^4$, $5\times10^4$, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$, $5\times10^{11}$, $1\times10^{12}$, $5\times10^{12}$, $1\times10^{13}$, $5\times10^{13}$, $1\times10^{14}$, or $5\times10^{14}$ spores/ml or spores/cm$^3$.

The particles can comprise at least about 40%, more preferably at least about 50% and less than 99.999% by weight of said particles of bacterial endospores.

Optionally, for any of the compositions disclosed herein, individual particles can have a mass of from about 1 mg to about 5000 mg, alternatively from about 5 mg to about 1000 mg, alternatively from about 5 mg to about 200 mg, alternatively from about 10 mg to about 100 mg, alternatively from about 20 mg to about 50 mg, alternatively from about 35 mg to about 45 mg, alternatively about 38 mg, alternatively combinations thereof and any whole numbers or ranges of whole numbers of mg within any of the aforementioned ranges. Particles having a mass in the aforesaid ranges can have dissolution times in water that permit the particles to dissolve during a typical wash cycle. In a plurality of particles, individual particles can have a shape selected from the group consisting of spherical, hemispherical, compressed hemispherical, lentil shaped, and oblong.

The plurality of particles can have a mean particle mass of from about 1 mg to about 5000 mg, alternatively from about 5 mg to about 1000 mg, alternatively from about 5 mg to about 200 mg, alternatively from about 10 mg to about 100 mg, alternatively from about 20 mg to about 50 mg, alternatively from about 35 mg to about 45 mg, alternatively about 38 mg. The plurality of particles can have standard deviation of mass of less than about 30 mg, alternatively less than about 15 mg, alternatively less than about 5 mg, alternatively about 3 mg. The mean particle of mass within the aforesaid ranges can provide for a dissolution time in water that permits the particles to dissolve during a typical wash cycle. Without being bound by theory, it is thought that particles have such a standard deviation of mass can have a more uniform dissolution time in water as compared to particles having a broader standard deviation of mass. The smaller the standard deviation of mass of the particles the more uniform the dissolution time. The mass of the individual particles forming the plurality particles can be set to provide the desired dissolution time, which might be some fraction of the length of the typical washing cycle in a washing machine. Particles formed from polyethylene glycol having a weight average molecular weight of about 9000 can have mean particle mass of about 38 mg and standard deviation of mass of about 3 mg.

An individual particle may have a volume from about 0.003 cm$^3$ to about 5 cm$^3$. An individual particle may have a volume from about 0.003 cm$^3$ to about 1 cm$^3$. An individual particle may have a volume from about 0.003 cm$^3$ to about 0.5 cm$^3$. An individual particle may have a volume from about 0.003 cm$^3$ to about 0.2 cm$^3$. An individual particle may have a volume from about 0.003 cm$^3$ to about 0.15 cm$^3$. Smaller particles are thought to provide for better packing of the particles in a container and faster dissolution in the wash.

The composition can comprise particles that are retained on a number 10 sieve as specified by ASTM International, ASTM E11-13. The composition can comprise particles wherein more than about 50% by weight of the particles are retained on a number 10 sieve as specified by ASTM International, ASTM E11-13. The composition can comprise particles wherein more than about 70% by weight of the particles are retained on a number 10 sieve as specified by ASTM International, ASTM E11-13. The composition can comprise particles wherein more than about 90% by weight of the particles are retained on a number 10 sieve as specified by ASTM International, ASTM E11-13. It can be desirable to provide particles sized as such because particles retained on a number 10 sieve may be easier to handle than smaller particles.

The composition can comprise particles that are retained on a number 6 sieve as specified by ASTM International, ASTM E11-13. The composition can comprise particles wherein more than about 50% by weight of the particles are retained on a number 6 sieve as specified by ASTM International, ASTM E11-13. The composition can comprise particles wherein more than about 70% by weight of the particles are retained on a number 6 sieve as specified by ASTM International, ASTM E11-13. The composition can comprise particles wherein more than about 90% by weight of the particles are retained on a number 6 sieve as specified by ASTM International, ASTM E11-13. It can be desirable to provide particles sized as such because particles retained on a number 6 sieve may be easier to handle than smaller particles.

The composition can comprise particles that pass a sieve having a nominal sieve opening size of 22.6 mm. The composition can comprise particles that pass a sieve having a nominal sieve opening size of 22.6 mm and are retained on a sieve having a nominal sieve opening size of 0.841 mm Particles having a size such that they are retained on a sieve having a nominal opening size of 22.6 mm may tend to have a dissolution time that is too great for a common wash cycle. Particles having a size such that they pass a sieve having a nominal sieve opening size of 0.841 mm may be too small to conveniently handle. Particles having a size within the aforesaid bounds may represent an appropriate balance between dissolution time and ease of particle handling.

Particles having the size disclosed herein can be substantial enough so that they do not readily become airborne when poured from a container, dosing cup, or other apparatus, into a wash basin or washing machine. Further, such particles as disclosed herein can be easily and accurately poured from a container into a dosing cup. So such particles make it easy for the consumer to control the amount of spores she delivers to the wash.

A plurality of particles may collectively comprise a dose for dosing to a laundry washing machine or laundry wash basin. A single dose of the particles may comprise from about 1 g to about 27 g of particles. A single dose of the particles may comprise from about 5 g to about 27 g, alternatively from about 13 g to about 27 g, alternatively from about 14 g to about 20 g, alternatively from about 15 g to about 19 g, alternatively from about 18 g to about 19 g, alternatively combinations thereof and any whole numbers of grams or ranges of whole numbers of grams within any of the aforementioned ranges. The individual particles forming the plurality of particles that can make up the dose can have a mass from about 1 mg to about 5000 mg, alternatively from about 5 mg to about 1000 mg, alternatively from about 5 mg to about 200 mg, alternatively from about 10 mg to about 100 mg, alternatively from about 20 mg to about 50 mg, alternatively from about 35 mg to about 45 mg, alternatively about 38 mg, alternatively combinations thereof and any whole numbers or ranges of whole numbers of mg within any of the aforementioned ranges. The plurality of particles can be made up of particles having different size, shape, and/or mass. The particles in a dose can each have a maximum dimension less than about 15 mm Each of the particles in a dose can have a maximum dimension less than about 1 cm.

The particles disclosed herein can be conveniently employed to treat laundry articles during a laundry process. The particles should be used in combination with a laundry detergent. The steps of the process can be to provide such particles comprising the formulation components disclosed herein. A dose of the particles can be placed in a dosing cup. The dosing cup can be the closure of a container containing the particles. The dosing cup can be a detachable and attachable dosing cup that is detachable and attachable to a container containing the particles or to the closure of such container. The dose of particles in the dosing cup can be dispensed into a washing machine. The step of dispensing the particles in the washing machine can take place by pouring the particles into the washing machine or placing the dosing cup and the particles contained therein into the washing machine, preferably the particles are dosed into the drum of an automatic laundry machine.

Carrier

By "non-germinant" carrier is herein meant a carrier that does not contribute to the germination of the endospores.

The carrier can be or comprise a material selected from the group consisting of water soluble inorganic alkali metal salt, water-soluble alkaline earth metal salt, water-soluble organic alkali metal salt, water-soluble organic alkaline earth metal salt, water soluble carbohydrate, water-soluble silicate, water soluble urea, and any combination thereof. Alkali metal salts can be, for example, selected from the group consisting of salts of lithium, salts of sodium, and salts of potassium, and any combination thereof. Useful alkali metal salts can be, for example, selected from the group consisting of alkali metal fluorides, alkali metal chlorides, alkali metal bromides, alkali metal iodides, alkali metal sulfates, alkali metal bisulfates, alkali metal phosphates, alkali metal monohydrogen phosphates, alkali metal dihydrogen phosphates, alkali metal carbonates, alkali metal monohydrogen carbonates, alkali metal acetates, alkali metal citrates, alkali metal lactates, alkali metal pyruvates, alkali metal silicates, alkali metal ascorbates, and combinations thereof.

Alkali metal salts can be selected from the group consisting of, sodium fluoride, sodium chloride, sodium bromide, sodium iodide, sodium sulfate, sodium bisulfate, sodium phosphate, sodium monohydrogen phosphate, sodium dihydrogen phosphate, sodium carbonate, sodium hydrogen carbonate, sodium acetate, sodium citrate, sodium lactate, sodium tartrate, sodium silicate, sodium ascorbate, potassium fluoride, potassium chloride, potassium bromide, potassium iodide, potassium sulfate, potassium bisulfate, potassium phosphate, potassium monohydrogen phosphate, potassium dihydrogen phosphate, potassium carbonate, potassium monohydrogen carbonate, potassium acetate, potassium citrate, potassium lactate, potassium tartrate, potassium silicate, potassium, ascorbate, and combinations thereof. Alkaline earth metal salts can be selected from the group consisting of salts of magnesium, salts of calcium, and the like, and combinations thereof. Alkaline earth metal salts can be selected from the group consisting of alkaline metal fluorides, alkaline metal chlorides, alkaline metal bromides, alkaline metal iodides, alkaline metal sulfates, alkaline metal bisulfates, alkaline metal phosphates, alkaline metal monohydrogen phosphates, alkaline metal dihydrogen phosphates, alkaline metal carbonates, alkaline metal monohydrogen carbonates, alkaline metal acetates, alkaline metal citrates, alkaline metal lactates, alkaline metal pyruvates, alkaline metal silicates, alkaline metal ascorbates, and combinations thereof. Alkaline earth metal salts can be selected from the group consisting of magnesium fluoride, magnesium chloride, magnesium bromide, magnesium iodide, magnesium sulfate, magnesium phosphate, magnesium monohydrogen phosphate, magnesium dihydrogen phosphate, magnesium carbonate, magnesium monohydrogen carbonate, magnesium acetate, magnesium citrate, magnesium lactate, magnesium tartrate, magnesium silicate, magnesium ascorbate, calcium fluoride, calcium chloride, calcium bromide, calcium iodide, calcium sulfate, calcium phosphate, calcium monohydrogen phosphate, calcium dihydrogen phosphate, calcium carbonate, calcium monohydrogen carbonate, calcium acetate, calcium citrate, calcium lactate, calcium tartrate, calcium silicate, calcium ascorbate, and combinations thereof. Inorganic salts, such as inorganic alkali metal salts and inorganic alkaline earth metal salts, do not contain carbon. Organic salts, such as organic alkali metal salts and organic alkaline earth metal salts, contain carbon. The organic salt can be an alkali metal salt or an alkaline earth metal salt of sorbic acid (i.e., asorbate). Sorbates can be selected from the group consisting of sodium sorbate, potassium sorbate, magnesium sorbate, calcium sorbate, and combinations thereof.

The carrier can be or comprise a material selected from the group consisting of a water-soluble inorganic alkali metal salt, a water-soluble organic alkali metal salt, a water-soluble inorganic alkaline earth metal salt, a water-soluble organic alkaline earth metal salt, a water-soluble carbohydrate, a water-soluble silicate, a water-soluble urea, and combinations thereof. The carrier or water soluble-soluble carrier can be selected from the group consisting of sodium chloride, potassium chloride, calcium chloride, magnesium chloride, sodium sulfate, potassium sulfate, magnesium sulfate, sodium carbonate, potassium carbonate, sodium hydrogen carbonate, potassium hydrogen carbonate, sodium acetate, potassium acetate, sodium citrate, potassium citrate, sodium tartrate, potassium tartrate, potassium sodium tartrate, calcium lactate, water glass, sodium silicate, potassium silicate, dextrose, fructose, galactose, isoglucose, glucose, sucrose, raffinose, isomalt, xylitol, candy sugar, coarse sugar, and combinations thereof. In one embodiment, the carrier or water-soluble carrier can be sodium chloride. In one embodiment, the carrier or water-soluble carrier can be table salt.

The carrier can be or comprise a material selected from the group consisting of sodium bicarbonate, sodium sulfate, sodium carbonate, sodium formate, calcium formate, sodium chloride, sucrose, maltodextrin, corn syrup solids, corn starch, wheat starch, rice starch, potato starch, tapioca starch, clay, silicate, citric acid carboxymethyl cellulose, fatty acid, fatty alcohol, glyceryl diester of hydrogenated tallow, glycerol, and combinations thereof.

The carrier can be selected from the group consisting of water soluble organic alkali metal salt, water soluble inorganic alkaline earth metal salt, water soluble organic alkaline earth metal salt, water soluble carbohydrate, water soluble silicate, water soluble urea, starch, clay, water insoluble silicate, citric acid carboxymethyl cellulose, fatty acid, fatty alcohol, glyceryl diester of hydrogenated tallow, glycerol, polyethylene glycol, and combinations thereof.

The carrier can be selected from the group consisting of disaccharides, polysaccharides, silicates, zeolites, carbonates, sulfates, citrates, and combinations thereof.

Examples of water soluble polymers include but are not limited to polyvinyl alcohols (PVA), modified PVAs; polyvinyl pyrrolidone; PVA copolymers such as PVA/polyvinyl pyrrolidone and PVA/polyvinyl amine; partially hydrolyzed polyvinyl acetate; polyalkylene oxides such as polyethylene oxide; polyethylene glycols; acrylamide; acrylic acid; cellulose, alkyl cellulosics such as methyl cellulose, ethyl cellulose and propyl cellulose; cellulose ethers; cellulose esters; cellulose amides; polyvinyl acetates; polycarboxylic acids and salts; polyaminoacids or peptides; polyamides; polyacrylamide; copolymers of maleic/acrylic acids; polysaccharides including starch, modified starch; gelatin; alginates; xyloglucans, other hemicellulosic polysaccharides including xylan, glucuronoxylan, arabinoxylan, mannan, glucomannan and galactoglucomannan; and natural gums such as pectin, xanthan, and carrageenan, locus bean, arabic, tragacanth; and combinations thereof. In one embodiment the polymer comprises polyacrylates, especially sulfonated polyacrylates and water-soluble acrylate copolymers; and alkylhydroxy cellulosics such as methylcellulose, carboxymethylcellulose sodium, modified carboxy-methylcellulose, dextrin, ethylcellulose, propylcellulose, hydroxyethyl cellulose, hydroxypropyl methylcellulose, maltodextrin, polymethacrylates. In yet another embodiment the polymer comprises PVA; PVA copolymers; hydroxypropyl methyl cellulose (HPMC); and mixtures thereof.

The particles can comprise at least 40%, preferably at least 50% and 99.999% or less, by weight of the particles of the carrier. The particles can comprise from about 45% by weight to about 99.999% by weight of the particles of the carrier. The particles can comprise from about 45% by weight to about 99.99% by weight of the particles of the carrier.

Preferably, the carrier is polyethylene glycol (PEG). PEG can be a convenient material to employ to make particles because it can be sufficiently water soluble to dissolve during a wash cycle when the particles are within the aforesaid range of mass. Further, PEG can be easily processed as melt. The melt temperature of PEG can vary as a function of molecular weight of the PEG. The melt temperature of PEG, depending on molecular weight and or distribution of molecular weight, can be low enough such that when the particles comprising PEG and bacterial endospores are formed from a melt that includes PEG and the endospores, the activity of the endospores remains high enough to be able to decrease malodor of fabrics.

The particles can comprise more than about 40% by weight PEG having a weight average molecular weight from about 2000 to about 13000. PEG has a relatively low cost, may be formed into many different shapes and sizes, minimizes unencapsulated perfume diffusion, and dissolves well in water. PEG comes in various weight average molecular weights. A suitable weight average molecular weight range of PEG includes from about 2,000 to about 13,000, from about 4,000 to about 12,000, alternatively from about 5,000 to about 11,000, alternatively from about 6,000 to about 10,000, alternatively from about 7,000 to about 9,000, alternatively combinations thereof. PEG is available from BASF, for example PLURIOL E 8000.

The particles can comprise more than about 40% by weight of the particles of PEG. The particles can comprise more than about 50% by weight of the particles of PEG. The particles can comprise more than about 60% by weight of the particles of PEG. The particles may comprise from about 65% to about 99% by weight of the composition of PEG. The particles may comprise from about 40% to about 99% by weight of the composition of PEG. The particles may comprise from about 45% to about 99% by weight of the composition of PEG.

The plurality of particles can be substantially free from particles having a mass less than about 10 mg. This can be practical for limiting the ability of the particles to become airborne.

Depending on the application, the particles can comprise from about 0.5% to about 5% by weight of the particles of a balancing agent selected from the group consisting of glycerin, polypropylene glycol, isopropyl myristate, dipropylene glycol, 1,2-propanediol, and PEG having a weight average molecular weight less than 2,000, and mixtures thereof. The balancing agent can be practical for providing particles having the same processing characteristics even though the particles have different formulations. For instance, two different scent variants of a product may have different levels of perfume. With use of a balancing agent, the PEG level can be the same in each scent variant and the formulas can be balanced with the balancing agent. This can make processing simpler in that the formulas for the scent variants will have the same level of PEG and may have similar processing characteristics.

The particles can comprise an antioxidant. The antioxidant can help to promote stability of the color and or odor of the particles over time between production and use. The particles can comprise between about 0.01% to about 1% by weight antioxidant. The particles can comprise between about 0.001% to about 2% by weight antioxidant. The particles can comprise between about 0.01% to about 0.1% by weight antioxidant. The antioxidant can be butylated hydroxytoluene.

Dye

The particles may comprise dye. The dye may include those dyes that are typically used in laundry detergent or fabric softeners. The fabric treatment composition may comprise less than about 0.1%, alternatively about 0.001% to about 0.1%, alternatively about 0.01% to about 0.02%, alternatively combinations thereof and any hundredths of percent or ranges of hundredths of percent within any of the aforementioned ranges, of dye by weight of the particles of fabric treatment composition. Examples of suitable dyes include, but are not limited to, LIQUITINT PINK AM, AQUA AS CYAN 15, and VIOLET FL, available from Milliken Chemical. Employing a dye can be practical to help the user differentiate between particles having differing scents.

Perfume

In addition to the carrier, the particles can further comprise 0.1% to about 20% by weight perfume. The perfume can be unencapsulated perfume, encapsulated perfume, perfume provided by a perfume delivery technology, or a perfume provided in some other manner Perfumes are generally described in U.S. Pat. No. 7,186,680 at column 10, line 56, to column 25, line 22. The particles can comprise unencapsulated perfume and are essentially free of perfume carriers, such as a perfume microcapsules. The particles can comprise perfume carrier materials (and perfume contained therein). Examples of perfume carrier materials are described in U.S. Pat. No. 7,186,680, column 25, line 23, to column 31, line 7. Specific examples of perfume carrier materials may include cyclodextrin and zeolites.

The particles can comprise about 0.1% to about 20%, alternatively about 1% to about 15%, alternatively 2% to about 10%, alternatively combinations thereof and any whole percentages within any of the aforementioned ranges, of perfume by weight of the particles. The particles can comprise from about 0.1% by weight to about 6% by weight of the particles of perfume. The perfume can be unencapsulated perfume and or encapsulated perfume.

The particles can be free or substantially free of a perfume carrier. The particles may comprise about 0.1% to about 20%, alternatively about 1% to about 15%, alternatively 2% to about 10%, alternatively combinations thereof and any whole percentages within any of the aforementioned ranges, of unencapsulated perfume by weight of the particles.

The particles can comprise unencapsulated perfume and perfume microcapsules. The particles may comprise about 0.1% to about 20%, alternatively about 1% to about 15%, alternatively from about 2% to about 10%, alternatively combinations thereof and any whole percentages or ranges of whole percentages within any of the aforementioned ranges, of the unencapsulated perfume by weight of the particles. Such levels of unencapsulated perfume can be appropriate for any of the particles disclosed herein that have unencapsulated perfume.

The particles can comprise unencapsulated perfume and a perfume microcapsule but be free or essentially free of other perfume carriers. The particles can comprise unencapsulated perfume and perfume microcapsules and be free of other perfume carriers.

The particles can comprise encapsulated perfume. Encapsulated perfume can be provided as plurality of perfume microcapsules. A perfume microcapsule is perfume oil enclosed within a shell. The shell can have an average shell thickness less than the maximum dimension of the perfume core. The perfume microcapsules can be friable perfume microcapsules. The perfume microcapsules can be moisture activated perfume microcapsules.

The perfume microcapsules can comprise a melamine/formaldehyde shell. Perfume microcapsules may be obtained from Appleton, Quest International, or International Flavor & Fragrances, or other suitable source. The perfume microcapsule shell can be coated with polymer to enhance the ability of the perfume microcapsule to adhere to fabric. This can be desirable if the particles are designed to be a fabric treatment composition. The perfume microcapsules can be those described in U.S. Patent Pub. 2008/0305982.

The particles can comprise about 0.1% to about 20%, alternatively about 0.1% to about 10%, alternatively about 1% to about 15%, alternatively 2% to about 10%, alternatively combinations thereof and any whole percentages within any of the aforementioned ranges, of encapsulated perfume by weight of the particles.

The particles can comprise perfume microcapsules but be free of or essentially free of unencapsulated perfume. The particles may comprise about 0.1% to about 20%, alternatively about 1% to about 15%, alternatively about 2% to about 10%, alternatively combinations thereof and any whole percentages within any of the aforementioned ranges, of encapsulated perfume by weight of the particles.

Method of Making Particles

The particles of the invention can be made using a similar process to that described in WO2017/156095 A1, page 18, line 14 to page 21, line 3.

EXAMPLES/COMBINATIONS

A. A composition comprising a plurality of particles, wherein said particles comprise:
from about 40% to about 99% by weight of said particles of a carrier; and
from about 0.0001% to about 5% by weight of a bacterial composition comprising bacterial endospores; and
wherein each of said particles has a mass between about 1 mg to about 5000 mg.

B. The composition according to Paragraph A, wherein each of said particles has a mass between about 5 mg and about 200 mg.

C. The composition according to Paragraph A or B, wherein the composition is a laundry additive composition.

D. The composition according to Paragraph A to C, wherein the composition comprises particles that pass a sieve having a nominal sieve opening size of 22.6 mm and are retained on a sieve having a nominal sieve opening size of 0.841 mm E. The composition according to any one of Paragraphs A to D, wherein said carrier is a water soluble polymer.

F. The composition according to any one of Paragraphs A to E, wherein said particles comprise from more than 45% to about 99% by weight of said particles of said carrier.

G. The composition according to any one of Paragraphs A to F, wherein said carrier and said bacterial endospores are substantially homogeneously mixed with one another.

H. The composition according to any one of Paragraphs A to G, wherein said endospore is in particulate form.

I. The composition according to any one of Paragraphs A to H, wherein said particles comprise from about 0.5% to less than 3% by weight of said particles of said bacterial endospores.

J. The composition according to any one of Paragraphs A to I wherein said particles comprise from about 0.1% to about 20% by weight perfume.

K. The composition according to any one of Paragraphs A to J, wherein said carrier is polyethylene glycol, wherein said polyethylene glycol has a weight average molecular weight from about 2000 to about 13000.

L. The composition according to any one of Paragraphs A to K, wherein said particles comprise from about 0.1% to about 10% by weight encapsulated perfume.

M. The composition according to any one of Paragraphs A to L, wherein said bacterial endospores comprise at least bacteria from the genus *Bacillus*.

N. The composition according to any one of Paragraphs A to M, wherein said plurality of particles is substantially free from particles having a mass less than about 10 mg.

O. The composition according to any one of Paragraphs A to N, wherein said carrier is selected from the group consisting of sucrose, sucrose bentonite, water soluble organic alkali metal salt, water soluble inorganic alkaline earth metal salt, water soluble organic alkaline earth metal salt, water soluble carbohydrate, water soluble silicate, water soluble urea, starch, clay, water insoluble silicate, citric acid carboxymethyl cellulose, fatty acid, fatty alcohol, glyceryl diester of hydrogenated tallow, glycerol, polyethylene glycol, and combinations thereof.

P. A process for treating laundry articles comprising the steps of:
providing particles comprising:
from about 40% to about 99% by weight of said particles of a carrier; and from about 0.0001% to about 5% by weight of a bacterial composition comprising bacterial endospores;
placing a dose of said particles in a dosing cup; and
dispensing said dose of said particles into a washing machine;
wherein each of said particles has a mass between about 1 mg to about 5000 mg.

Q. The process according to Paragraph P, wherein said carrier is polyethylene glycol, wherein said polyethylene glycol has a weight average molecular weight from about 2000 to about 13000.

R. A process for forming particles comprising the steps of:
providing a precursor material;
providing a distributor having a plurality of apertures;
passing said precursor material through said apertures;
providing a moving conveyor beneath said distributor;
depositing said precursor material onto said moving conveyor; and
cooling said precursor material to form a plurality of particles;

wherein said precursor material comprises polyethylene glycol, wherein said polyethylene glycol has a weight average molecular weight from about 2000 to about 13000;
wherein said precursor material comprises from about 0.0001% to about 5% by weight of said precursor material of a bacterial composition comprising bacterial endospores; and
wherein said precursor material is provided at a temperature less than about 70° C.

Example 1: Preparation of Spores

Bacteria from which spores were to be prepared were grown logarithmically in liquid culture. As carbon, nitrogen, and/or phosphorus in the logarithmic cultures became limiting (e.g., late in logarithmic growth), the vegetative cells began to sporulate. The cultures continued to be incubated until it was estimated that no additional spores would form in the cultures. In some cases, the spores were obtained from cultures that were production runs. The cultures were then centrifuged to pellet the spores, and remaining cells and debris. When these spore pellets were suspended in water, washed, again suspended in water, and the spore suspension allowed to settle in a tube, three visible layers generally formed. Microscopic examination of samples was used to confirm the presence of phase-bright spores at a desired purity (>99% phase-bright spores). If purity was not achieved, then water washing was repeated until desired purity was reached.

Example 2: Preparation of PEG 8000 Particles with *Bacillus* sp. Endospores

To make a small batch of PEG 8000 particles containing *Bacillus* Spores powder, the following procedure was followed. About 100 g of PEG (Pluriol E 8000) was weighed and melted at 80° C. in the oven. To the melt, pre-weighed 0.01 grams of *Bacillus* spore powder was added (for Composition 1, nil Spores for Composition 2) to deliver $1.0 \times 10^8$ colony forming units (CFUs) of *Bacillus* spores and mixed for 30 seconds at 3500 rpm using Flacktek speed mixer. Under a sterile condition and in a Biosafety Cabinet, the hot PEG melt spore mixture was transferred to particle template using a sterile spatula and spread uniformly on the template. The composition mixture was cooled down to room temperature for approximately 5 min to form solid particles. The solidified particles were scraped off from the template and transferred to a sterile container for storage until needed.

TABLE 1

| | Ingredients | Activity | % FP Active | Through the Wash (TTW) Concentration (ppm) | *Bacillus* spores (CFUs) | Target (g) | CFUs/ 100 g spore beads |
|---|---|---|---|---|---|---|---|
| Composition 1 | Pluriol E 8000 | 100 | 99.990 | 271.923 | — | 99.99 | — |
| | *Bacillus* Spores powder | 100 | 0.010 | 0.027 | $1.75 \times 10^7$ | 0.01 | $1.0 \times 10^8$ |
| Composition 2 | Pluriol E 8000 | 100 | 100.0 | 271.923 | 0.00 | 100.00 | 0.00 |

Example 3: Viability of PEG 8000 Particles with *Bacillus* sp. Endospore

The Heat shock method and spore enumeration procedure was used to assess the viability and survivability of the spores during the process of making in the hot PEG8000 melt, during mechanical high-speed mixing and granulating on the bead template.

Spore suspension sample: The Composition 1 comprised of PEG 8000 particles with *Bacillus* spore and Composition 2 comprising of PEG 8000 particles only were each aseptically drawn and separately measured to 1 gram of the particle composition and each transferred into a tube containing 9 mL of sterile Saline (0.85% NaCl). The tube was vortexed for approximately 30 seconds to disperse the spores and to reconstitute into a homogeneous solution.

Heat Shock and enumeration of spores. The spore suspension sample was placed in 80° C. water bath for 15 min to stimulate germination of the spores and to kill any vegetative cells present. After heat treatment, the suspension was cooled in a crushed ice water bath and immediately placed in −20° C. freezer for 15 min. Then the samples were brought to room temperature before use. Then the Heat socked samples were aseptically measured and serially diluted by transferring 1 mL aliquots into 9 mL of sterile Saline to make to $10^{-1}$-$10^{-7}$). One-millilitre aliquots (1 ml) of the $10^{-1}$, $10^{-3}$, $10^{-5}$ and $10^{-7}$ dilutions was pour-plated onto separate solid nutrient growth media plates (Tryptic Soy Agar-TSA) via sterile inoculating loops. The TSA growth plates were incubated at 37° C. temperature for 24-48 hours and enumerated *Bacillus* colonies manually. Only the plates with 25-250 colonies were counted for statistical representation. The *Bacillus* colonies recovered from the particles was comparable (within ±10%) to that listed by the supplier. The viability and the levels of the *Bacillus* spores in the powder after heat shock process was comparable to one listed on the supplier's label and equal to the adjusted amount added into the hot PEG melt. The process of formulating the beads with *Bacillus* spores had no negative impact on the integrity of the spores and the stability of the spores in the bead over the 4 months was between 8.04-8.48 Log with SD below ±0.5 Log compared to actual spores count in the spore powder mix as shown in the Table 2.

TABLE 2

| | Raw Count | Cfu/mL | Log Cfu/mL |
|---|---|---|---|
| *Bacillus* Spore powder | As listed on the label | 1.63E+11 | 11.21 |
| | Actual spore powder mix | 1.62E+08 | 8.21 |
| Composition 1: (PEG 8000 particles with Spore at Dilution ($10_{-7}$) | Month 1 | 3.00E+08 | 8.48 |
| | Month 2 | 1.20E+08 | 8.08 |
| | Month 3 | 1.94E+08 | 8.29 |
| | Month 4 | 1.10E+08 | 8.04 |
| Composition 2: (PEG 8000 particles with nil Spore at Dilution ($10_{-7}$) | No count | 0.00E+00 | 0.00 |

Malodour Tests
Direct application of spore powder in phosphate buffer
The malodour removal of spore powder applied directly on different items is shown in the table below.

| % Spores in PBS buffer Solution (pH 7.4) | Consumer Item (3" × 2" Swatches) | Time of Assessment after Treatment | | |
|---|---|---|---|---|
| | | 24 hr | 48 hr | 96 hr |
| 0.0001% eq. to $1.0 \times 10^6$ CPUs *Bacillus* spores | Polycotton T-shirts | 1.0 | 4.0 | 0.5 |
| | Bath Towels | 3.5 | 1.5 | 0.5 |
| Nil spores (PBS only) | Polycotton & Towels | 5.0 | 5.0 | 5.0 |

Malodor Intensity Scale (0-5) where, 0 = No malodor, 0.5 = Slight malodor, 1 = Noticeable malodor, 2= Very noticeable malodor, 3 = Very Noticeable malodor, 4 = Strong malodor, 5 = Very Strong/Intense malodor Spore powder was made in phosphate buffer saline (PBS pH 7.4) solution and applied directly onto preselected swatches (5×5 Inches) of polycotton T-shirts and bath towels with very intense malodor. The control test solution comprised of PBS application only (nil spores). The fabrics were incubated at 37° C. and after every time point of treatment, the fabrics were washed in Tide Free (nil perfume) detergent, then dried and rebloomed to assess the malodor. The direct application tests with spores showed noticeable malodor reduction at all time points with highly noticeable malodor reduction at 96 hr compared to the controls.

Through the Wash (TTW) Application of the Particles of the Invention

The malodour removal of the particles of the invention used in a laundry process on bath towels is showed in the below table.

| Consumer bath towel 3" × 2" swatches with extremely intense malodor | Time of Assessment after Treatment | | |
|---|---|---|---|
| | 24 hr | 48 hr | 144 hr |
| Test: Spore beads (0.055 ppm) eq. to $5.5 \times 10^6$ CPUs | 63.6% | 33.3% | 36.4% |
| Control: No spore beads (0 ppm) | 36.4% | 66.7% | 63.6% |
| N = Number of Judge volunteers | 11 | 9 | 11 |

Malodor assessment: Volunteer judges were asked to select the bath towel with the more malodor in a pair comparison test
The higher the % of the judges = high malodor Spore powder was made into PEG 8000 particles. The Spore particles finished product (FP) contained 0.01% spores powder equivalent to 100 ppm corresponding to $1.0\times10^8$ total CFUs of the *Bacillus* spores. A bath towel with intense malodor was cut into swatches and washed in Fast Wash with Tide free detergent and spore beads at dosage to deliver through the wash concentration at 0.055 ppm equivalent to $5.5\times10^6$ CFUs of spores through the wash while the control test was washed with Tide Free detergent only. The bath towel swatches were incubated at 37° C. and after every time point the swatches were rebloomed for olfactive assessment by volunteers familiar with bath towel malodor. The judges were asked to select the bath towel with intense malodor.

Example 4: Through the Wash (TTW) Application of Particles of the Invention

Pyrex crystal particles, non-ionic surfactant particles and sodium acetate particles were made in a similarly manner to the PEG 8000 particles of Example 2. The malodour removal of the particles used in a laundry process on bath towels is showed in the below table.

| Consumer bath towel 3" × 2" swatches with High-to-Very Intense malodor | | | Time of Assessment after Treatment | | | | |
|---|---|---|---|---|---|---|---|
| | | Through the Wash Conc. | (Average Malodor Score = Total Mal Score/N) | | | | |
| Particle Type | Ingredients (% w/w) | Spores (ppm)/ CFU equivalent | 24-hr | 48-hr | 72-hr | 96-hr | Malodor Reduction Benefit (Y/N) |
| PEG 8000 + Spores | 99.99% PEG 8000 + 0.01% Spores | 0.055 ppm/eq. to $5.5 \times 10^6$ CFUs | 2.3 | 1.5 | 1.9 | 1.0 | Yes |
| PEG 8000 | 100% PEG 8000 + 0.0% Spores | 0.00 ppm/eq. to 0.0 CFUs | 3.5 | 2.5 | 2.4 | 4.5 | None |

-continued

| Consumer bath towel 3" × 2" swatches with High-to-Very Intense malodor | | Time of Assessment after Treatment | | | | |
|---|---|---|---|---|---|---|
| | Through the Wash Conc. | (Average Malodor Score = Total Mal Score/N) | | | | |
| Particle Type | Ingredients (% w/w) | Spores (ppm)/ CFU equivalent | 24-hr | 48-hr | 72-hr | 96-hr | Malodor Reduction Benefit (Y/N) |
| Pyrex Crystals + Spores | 15% PEG 4000//10% Bentonite//74.99% NaCl + 0.01% Spores | 0.055ppm/eq. to 5.5 × $10^6$ CFUs | 1.8 | 2.6 | 1.6 | 1.0 | Yes |
| Pyrex Crystals | 15% PEG 4000//10% Bentonite//75%NaCl + 0.0% Spores | 0.00 ppm/eq. to 0.0 CFUs | 3.0 | 3.8 | 3.4 | 5.0 | None |
| Pluronic F-127 + Spores | 99.99% Pluronic F-127 + 0.01% Spores | 0.055 ppm/eq. to 5.5 × $10^6$ CFUs | 2.0 | 1.4 | 1.3 | 1.0 | Yes |
| Pluronic F-127 | 100% Pluronic F-127 + 0.0% Spores | 0.00 ppm/eq. to 0.0 CFUs | 2.3 | 3.3 | 3.4 | 5.0 | None |
| Sodium Acetate Chassis + Spores | 70.79% Sodium Acetate//29.20% Exilva FO3 (Forte 2%) + 0.01% Spores | 0.055 ppm/eq. to 5.5 × $10^6$ CFUs | 1.8 | 1.7 | 1.6 | 1.0 | Yes |
| Sodium Acetate Chassis | 70.80% Sodium Acetate//29.20% Exilva FO3 (Forte 2%) + 0.0% Spores | 0.00 ppm/eq. to 0.0 CFUs | 3.5 | 3.8 | 3.3 | 4.5 | None |
| Number of Judge volunteers | | N/a | N = 5 | N = 5 | N = 6 | N = 5 | N/a |

Malodor assessment: Volunteer judges were asked to select the bath towel with high malodor in a pair comparison test and assign a malodor score on a scale of 1-5 to the pair (Average score is reported)
1 = Low-to-No Malodor,
2 = Low-to-Medium Malodor,
3 = Medium-to-High Malodor,
4 = High-to-Intense Malodor,
5 = Very High and Intense Malodor The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition comprising a plurality of particles, wherein said particles comprise:
a non-germinant carrier comprising at least about 40% by weight of the particles of polyethylene glycol having a weight average molecular weight from about 2000 to about 13000; and
from about 0.0001% to about 5% by weight of said particles of a bacterial composition comprising bacterial endospores,
wherein the non-germinant carrier and the bacterial composition are substantially homogeneously mixed with one another; and
wherein each of said particles has a mass between about 5 mg and about 200 mg.

2. The composition according to claim 1 wherein the bacterial composition comprises bacterial endospores in a level of from about $1\times10^2$ to about $1\times10^9$ CFU/g of particle.

3. The composition according to claim 1 wherein the bacterial composition comprises bacterial endospores in a level of from about $1\times10^3$ to about $1\times10^6$ CFU/g of particle.

4. The composition according to claim 1 wherein the endospores comprise bacteria from the genus *Bacillus*.

5. The composition according to claim 1 wherein the endospores comprise bacteria selected from the group consisting of *Bacillus subtilis, Bacillus atnyloligKfaciens, Bacillus licheniformis, Bacillus megaterium, Bacillus pumilus* and mixtures therein.

6. The composition according to claim 1 wherein the carrier further comprises a carrier selected from the group consisting of sucrose, bentonite, water soluble organic alkali metal salt, water soluble inorganic alkaline earth metal salt, water soluble organic alkaline earth metal salt, water soluble carbohydrate, water soluble silicate, water soluble urea, starch, clay, water insoluble silicate, citric acid, glycolic acid, carboxymethyl cellulose, fatty acid, fatty alcohol, glyceryl diester of hydrogenated tallow, glycerol, polyvinyl alcohol and combinations thereof.

7. The composition according to claim 1 wherein the particles comprise from about 0.1% to about 20% by weight of perfume.

8. The composition according to claim 1 wherein the plurality of particles is substantially free from particles having a mass of less than about 10 mg.

9. A product comprising a container and a composition according to claim 1.

10. A process for forming particles comprising the steps of:
providing a precursor material;
providing a distributor having a plurality of apertures;
passing said precursor material through said apertures;
providing a moving conveyor beneath said distributor;
depositing said precursor material onto said moving conveyor; and
cooling said precursor material to form a plurality of particles;
wherein said precursor material comprises polyethylene glycol, wherein said polyethylene glycol has a weight average molecular weight from about 2000 to about 13000;
wherein said precursor material comprises from about 0.0001% to about 5% by weight of said precursor material of a bacterial composition comprising bacterial endospores; and
wherein said precursor material is provided at a temperature less than about 70° C.

11. The composition of claim 1, wherein the non-germinant carrier comprises a polyethylene glycol with a weight average molecular weight of about 8000, a polyethylene glycol with a weight average molecular weight of about 4000, or a combination thereof.

12. A composition comprising a plurality of particles, wherein said particles comprise:
about 40% to about 99% by weight of the composition of polyethylene glycol having a weight average molecular weight from 2000 to about 13000; and
from about 0.0001% to about 5% by weight of said particles of a bacterial composition comprising bacterial endospores;
wherein the polyethylene glycol and the bacterial composition are substantially homogeneously mixed with one another; and
wherein the particles have a size such that said particles will pass through a sieve with an opening size of 22.6 mm.

13. The composition of claim 12, wherein the particles have a size such that they are retained on sieve having an opening size of about 0.841 mm.

14. The composition of claim 12, wherein the polyethylene glycol comprises a polyethylene glycol with a weight average molecular weight of about 8000, a polyethylene glycol with a weight average molecular weight of about 4000, or a combination thereof.

* * * * *